US007015490B2

(12) United States Patent
Wang et al.

(10) Patent No.: US 7,015,490 B2
(45) Date of Patent: Mar. 21, 2006

(54) METHOD AND APPARATUS FOR OPTIMIZATION OF COLLIMATOR ANGLES IN INTENSITY MODULATED RADIATION THERAPY TREATMENT

(75) Inventors: Duan Qiang Wang, Carmel, IN (US); Robert W. Hill, Washington, PA (US); Simon Chun-pin Lam, Phoenix, AZ (US)

(73) Assignee: Nomos Corporation, Cranberry Township, PA (US)

( * ) Notice: Subject to any disclaimer, the term of this patent is extended or adjusted under 35 U.S.C. 154(b) by 0 days.

(21) Appl. No.: 10/915,968

(22) Filed: Aug. 11, 2004

(65) Prior Publication Data

US 2005/0123098 A1     Jun. 9, 2005

Related U.S. Application Data

(60) Provisional application No. 60/494,222, filed on Aug. 11, 2003.

(51) Int. Cl.
*A61N 5/10* (2006.01)
*G21K 1/02* (2006.01)

(52) U.S. Cl. .................... 250/505.1; 378/150
(58) Field of Classification Search .............. None
See application file for complete search history.

(56) References Cited

U.S. PATENT DOCUMENTS

| | | | | |
|---|---|---|---|---|
| 4,672,212 A | * | 6/1987 | Brahme | 250/505.1 |
| 5,596,619 A | * | 1/1997 | Carol | 378/65 |
| 5,802,136 A | * | 9/1998 | Carol | 378/65 |
| 5,818,902 A | | 10/1998 | Yu | |
| 6,393,096 B1 | * | 5/2002 | Carol et al. | 378/65 |
| 6,907,105 B1 | * | 6/2005 | Otto | 378/65 |
| 2003/0086530 A1 | | 5/2003 | Otto | |
| 2004/0190680 A1 | * | 9/2004 | Chang | 378/65 |
| 2005/0111621 A1 | * | 5/2005 | Riker et al. | 378/65 |

OTHER PUBLICATIONS

Du M N et al., article titled "A Multileaf Collimator Field Prescription Preparation System For Conventional Radiotherapy," International Journal of Radiation Oncology Biology Physics UK, vol. 32, No. 2, 1995, pp. 513-520 (1995).
Shephard D M et al., articled titled "Direct aperture optimization: A turnkey solution for step-and-shoot IMRT," Medical Physics, American Institute of Physics, New York, US, vol. 29, No. 6, Jun. 2002, pp. 1007-1018, XP012011807 ISSN: 0094-2405.
Beavis A W et al., article titled "Optimisation of MLC orientation to improve accuracy in the static field delivery of IMRT," Proceedings of the 22nd Annual International Conference of the IEEE Engineering in Medicine and Biology Society (CAT. No. 00CH37143) IEEE Piscataway, NJ, USA, vol. 4, Jul. 2000, pp. 3086-3089 vol., XP002308750 ISBN.

(Continued)

*Primary Examiner*—Jack I. Berman
(74) *Attorney, Agent, or Firm*—Bracewell & Giuliani, LLP

(57) ABSTRACT

A method and apparatus to determine an optimum collimator angle of a multi-leaf collimator having an opening and multiple leaf pairs for closing portions of the opening to form a radiation beam arrangement having multiple radiation beam segments. The method and apparatus include application of a cost function to determine a collimator angle which provides for delivery efficiency and target conformity. The user can preferentially either selectively enhance delivery efficiency of the radiation beam arrangement, reducing a number of radiation beam segments and reducing a number of radiation beam monitor units required for delivery of the desired prescription, or selectively enhance conformity of the radiation beam arrangement to a target shape. The optimum collimator angle is then used for delivery of an optimized radiation beam arrangement to a patient by a radiation delivery device.

21 Claims, 10 Drawing Sheets

OTHER PUBLICATIONS

Frazier A et al., article titled "Dosimetric Evaluation of the Conformation of the Multileaf Colliomator to Irregularly Shaped Fields," International Journal of Radiation Oncology Biology Physics Elsevier UK, vol. 33, No. 5, 1995, pp. 1229-1238, XP002308751 ISSN: 0360-3016.

Wang et al., article titled "A New Algorithm for Determining Collimator Angles that Favor Efficiency in MLC based IMRT Delivery," Medical Physics AIP for American Assoc. Phys. Ed. USA, vol. 31, No. 5, Apr. 23, 2004, pp. 1249-1253, XP002308753 ISSN: 0094-2405, the whole document.

Samuelsson A et al., article titled "Intensity modulated radiotherapy treatment planning for dynamic multileaf collimator delivery: influence of different parameters on dose distributions," Radiotherapy and Oncology Elsevier Ireland, vol. 66, No. 1, Jan. 2003, pp. 19-28, XP002308752 ISSN: 0167-8140.

* cited by examiner

FIG. 1
(PRIOR ART)
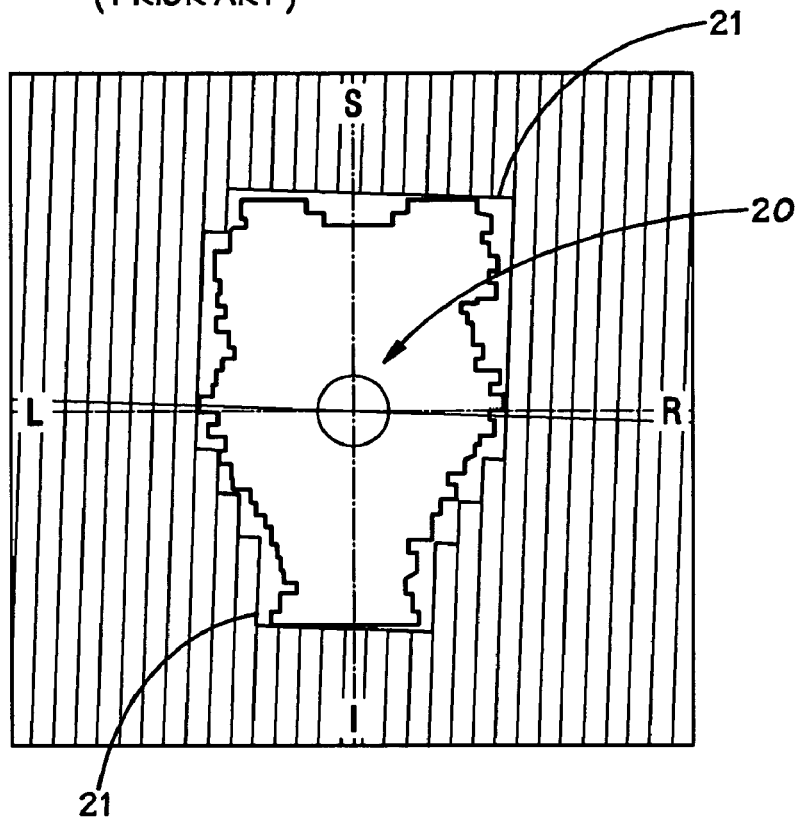
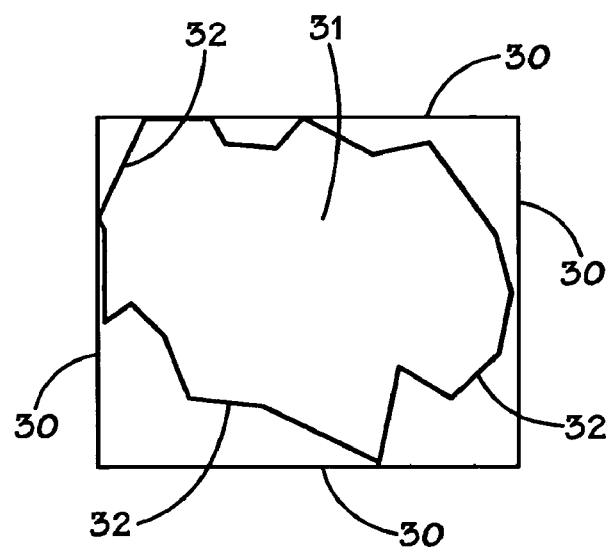
FIG. 2

FIG. 8

| SEQUENCING ALGORITHM | STANDARD 0.5 x 0.5 cm² | | STANDARD 1 x 1 cm² | | IMFAST 1 x 1 cm² | |
|---|---|---|---|---|---|---|
|  | NO. SEG. | MUs | NO. SEG. | MUs | NO. SEG. | MUs |
| $\theta$ SET AT WHERE $l_e$ IS A MIN. | 624 | 3218 | 192 | 1123 | 98 | 1702 |
| $\theta$ SET AT WHERE $l_e$ IS A MAX. | 945 | 4327 | 253 | 1526 | 105 | 1543 |
| RATIO (%) | 66 | 74 | 76 | 74 | 93 | 110 |

FIG. 9

| SEQUENCING ALGORITHM | STANDARD 0.5 x 0.5 cm² | | STANDARD 1 x 1 cm² | | IMFAST 1 x 1 cm² | |
|---|---|---|---|---|---|---|
|  | NO. SEG. | MUs | NO. SEG. | MUs | NO. SEG. | MUs |
| $\theta$ SET AT WHERE $l_e$ IS A MIN. | 286 | 1970 | 84 | 804 | 50 | 921 |
| $\theta$ SET AT WHERE $l_e$ IS A MAX. | 380 | 3183 | 91 | 802 | 59 | 981 |
| RATIO (%) | 75 | 62 | 92 | 101 | 85 | 94 |

| MLC TYPE | PROSTATE CI | | SEMINAL VESICLES CI | |
|---|---|---|---|---|
| | BRAHME'S | NEW ALGORITHM | BRAHME'S | NEW ALGORITHM |
| VARIAN 120 (V 120) | 0.9094 | 0.9566 | 0.9401 | 0.9600 |
| VARIAN 80 (V 80) | 0.8713 | 0.9429 | 0.9281 | 0.9688 |
| SIEMENS 54 (S 54) | 0.8748 | 0.9286 | 0.9108 | 0.9388 |
| ELEKTA 40 (E 40) | 0.9748 | 0.9829 | 0.9681 | 0.9451 |

METHOD AND APPARATUS FOR OPTIMIZATION OF COLLIMATOR ANGLES IN INTENSITY MODULATED RADIATION THERAPY TREATMENT

RELATED APPLICATIONS

This application claims the benefit of and priority to U.S. Provisional Patent Application Ser. No. 60/494,222 filed Aug. 11, 2003, entitled "Method and Apparatus for Optimization of Collimator Angles in Intensity Modulated Radiation Therapy Treatment."

INFORMATION INCORPORATED BY REFERENCE

Applicant incorporates by reference U.S. Pat. No. 5,596,619, entitled "Method and Apparatus for Conformal Radiation Therapy", issued Jan. 21, 1997, and U.S. Pat. No. 5,802,136, entitled "Method and Apparatus for Conformal Radiation Therapy", issued Sep. 1, 1998, which are both commonly assigned to the assignee of the present invention.

BACKGROUND OF THE INVENTION

1. Field of the Invention

The invention relates to a method and apparatus for intensity modulated radiation therapy treatment, and more specifically, a method and apparatus for optimization of collimator angles for multileaf collimators ("MLC") used in intensity modulated radiation therapy treatment.

2. Description of the Related Art

When determining collimator angles in intensity modulated radiation therapy treatment, or intensity modulated radiotherapy, ("IMRT") inverse treatment plans for use with a MLC radiation delivery system, the most common practice currently is to select collimator rotation angles so that the MLC can be best conformed to the shape of the target, or lesion, in the radiation beam's eye view, or beams eye view ("BEV"). The algorithm used is based upon Brahme's orientation theory, by which the conformity for targets is prioritized. When using this algorithm, no consideration is given to delivery efficiency, e.g., reduction of the number of segments and monitor units ("MU"). Note, the beams eye view is a view from the perspective of the opening in the multi-leaf collimator along an axis of the radiation beam. Note also, the number of segments are considered reduced when adjacent segments have substantially the same intensity level. A reduction in MU's is a reduction in the amount of radiation delivered to the target.

Accordingly, prior to the development of the present invention, there has been no method or apparatus for determining the collimator angle before optimization in inverse treatment planning system, which favors, or enhances delivery efficiency, such as by reducing the number of segments and MUs.

Therefore, the art has sought a method and apparatus for determining the collimator angle before optimization in an inverse treatment planning system which favors, or enhances, the delivery efficiency by reducing the number of segments and MUs.

SUMMARY OF THE INVENTION

In accordance with the invention, the foregoing advantages have been achieved through the present method and apparatus for optimization of collimator angles in IMRT inverse treatment planning systems. Embodiments of the present invention utilize a new algorithm to determine collimator angles in favoring, or enhancing, IMRT radiation therapy treatment plan delivery efficiency. The number segments and MUs can be reduced using the set of collimator angles determined by utilizing the new algorithm, without compromising treatment plan quality. Embodiments of the present invention also include a cost function obtained by combining the prior algorithm based upon Brahme's orientation theory with the algorithm utilized in the present invention. Through use of embodiments of the present invention, including utilizing the new algorithm, the number of segments and MUs may be reduced, particularly for IMRT treatment planning systems currently in use. Advantageously, embodiments of the present invention include a method and apparatus that provide benefits to certain MLCs currently in use, since the method and apparatus of the present invention seek to minimize the maximum travel distance of MLC leaf pairs.

More specifically, in embodiments of the present invention advantageously methods are provided to determine a collimator angle of a multi-leaf collimator having an opening and a plurality of multi-leaf collimator pair leafs for closing portions of the opening to form a radiation beam arrangement having a plurality of radiation beam segments to apply radiation to a tumor target. For example, an embodiment of the present convention includes a method, preferably being computer-implemented, which includes calculating an initial radiation beam arrangement according to a desired prescription to determine a radiation beam delivery angle (gantry angle of rotation for a linear accelerator). This radiation beam arrangement is updated or changed by incorporating a first function, generally in the form of a cost function, to determine an optimum collimator angle of the multi-leaf collimator. The first cost function includes both a second cost function designed to enhance delivery efficiency by reducing at least one of a number of radiation beam segments and reducing a number of radiation beam monitor units required for delivery of the desired prescription, and a third cost function to enhance conformity of the radiation beam arrangement to a target shape as viewed through the opening in the multi-leaf collimator. This view from the perspective of the opening in the multi-leaf collimator along an axis of the radiation beam defines a beams eye view of the multi-leaf collimator.

Advantageously, the collimator angle selection need not stop at the first iteration of computing the first function. The change or update in the radiation beam arrangement can be rejected if the change of the radiation beam arrangement significantly leads to a lesser correspondence to the desired prescription. For such occurrence, weights applied to the second and third functions can be adjusted. The change or update of the radiation beam arrangement, however, is generally accepted if the change of the radiation beam arrangement both leads to more radiation delivery efficiency and does not lead to significantly less correspondence to the desired prescription.

Also for example, in an embodiment of the present convention, a method includes first determining a treatment plan according to a desired prescription. A value of an area difference between an area of the opening in the multi-leaf collimator which the multi-leaf collimator can define when approaching correspondence with the target shape in the beams eye view of the multi-leaf collimator and an area of the target shape in the same beams eye view of the multi-leaf collimator is then determined for each one of a plurality of discrete collimator angles. A value of a maximum effective length for a multi-leaf collimator pair leaf of the plurality of multi-leaf collimator pair leafs having the maximum effective length can also be determined for each one of the plurality of discrete collimator angles. A sum of the value of the area difference and the value of the maximum effective length for each of the plurality of discrete collimator angles is then determined. A minimum sum value for the sum of the value of the area difference and the value of the maximum effective length for the collimator angle of the plurality of collimator angles having the minimum sum value, is then further determined. An analysis utilizing this function leads to the identification of the collimator angle best suited for application to the treatment plan prior to treatment plan optimization.

Depending upon the type or model of radiation delivery system carrying the multi-leaf collimator, the size and shape of the target, and/or whether efficiency or conformity or an intermediate mix thereof are assigned priority, weights can be assigned to the maximum effective length and area difference. By applying a first weight value to the maximum effective length and a second weight value to the area difference prior to determining the minimum sum value, a different collimator angle can be deemed the optimum angle.

In an embodiment of the present invention, a similar method includes providing a function, preferably in the form of a cost function, having a first delivery efficiency portion providing for enhanced radiation delivery efficiency and a second target conformity portion providing for enhanced target conformity. After preferably determining a type of radiation delivery system carrying the multi-leaf collimator and determining a size and a shape of the target, a preference can be selected between delivery efficiency and target conformity by assigning weights to the delivery efficiency and target conformity portions of the function. That is, the first delivery efficiency portion of the function includes a delivery efficiency function that determines at each of a plurality of discrete collimator angles a weighted value of a maximum effective length for a multi-leaf collimator pair leaf of the plurality of multi-leaf collimator pair leafs having the maximum effective length. The second target conformity portion of the function includes a target conformity function that determines at each of a plurality of discrete collimator angles a weighted value of an area difference between an area of the opening in the multi-leaf collimator which the multi-leaf collimator can define when approaching correspondence with the target shape in the beams eye view of the multi-leaf collimator and an area of the target shape in the beams eye view of the multi-leaf collimator.

A value for the cost function at a selected radiation beam delivery angle incorporating the selected preference is then determined. Determination of the function value directly leads to the determination of the optimum collimator angle at this given radiation beam delivery angle. Because a target is typically treated utilizing multiple radiation beam delivery angles (gantry angles of rotation on a linear accelerator), this process of determining an optimum collimator angle can be repeated for each selected radiation beam delivery angle.

Advantageously, an embodiment of the present invention, can be in the form of a computer readable medium that is readable by a computer determining a collimator angle of a multi-leaf collimator having an opening and a plurality of multi-leaf collimator pair leafs for closing portions of the opening to form a radiation beam arrangement having a plurality of radiation beam segments to apply radiation to a tumor target. The computer readable medium includes a set of instructions that, when executed by the computer, causes the computer to perform various operations such as determining a treatment plan according to a desired prescription, determining for each one of a plurality of discrete collimator angles a value of an area difference between an area of the opening in the multi-leaf collimator which the multi-leaf collimator can define when approaching correspondence with the target shape in the beams eye view of the multi-leaf collimator and an area of the target shape in the same beams eye view of the multi-leaf collimator, and determining for each one of the plurality of discrete collimator angles a value of a maximum effective length for a multi-leaf collimator pair leaf of the plurality of multi-leaf collimator pair leafs having the maximum effective length. The instructions can also include determining a sum of the value of the area difference and the value of the maximum effective length for each of the plurality of discrete collimator angles, and a minimum sum value for the sum of the value of the area difference and the value of the maximum effective length for the collimator angle of the plurality of collimator angles having the minimum sum value. This determination allows for the selection of an optimum collimator angle for application to the treatment plan, typically implemented prior to treatment plan optimization.

Advantageously, embodiments of the present invention also include an apparatus for use in conformal radiation therapy of a target tumor. The apparatus can include a multi-leaf collimator having a plurality of selectable discrete collimator angles, an opening to pass a radiation beam, and a plurality of multi-leaf collimator pair leafs to close portions of the opening to form a radiation beam arrangement having a plurality of radiation beam segments. The apparatus can also include a computer in communication with the multi-leaf collimator to form the radiation beam arrangement incorporating a function to determine a collimator angle of the multi-leaf collimator to thereby enhance the radiation beam arrangement. The function includes parameters to enhance delivery efficiency by reducing a number of segments and reducing a number of monitor units required for delivery of a desired radiation prescription. These parameters can include a value of a maximum effective length for a multi-leaf collimator pair leaf of the plurality of multi-leaf collimator pair leafs having the maximum effective length. The function can also include parameters to enhance conformity of the radiation beam arrangement to a shape of the target as viewed through the opening in the multi-leaf collimator, a view from the perspective of the opening in the multi-leaf collimator along an axis of the radiation beam defining a beams eye view of the multi-leaf collimator. These parameters can include a value of an area difference between an area of an opening in the multi-leaf collimator which the multi-leaf collimator can define when approaching correspondence with a target shape in the beams eye view of the multi-leaf collimator and an area of the target shape in the beams eye view of the multi-leaf collimator. The apparatus can further include means for selecting a first weight value for the maximum effective length and a second weight value for the area difference, and means for applying the first weight value to the maximum effective length and the second weight value to the area difference prior to determining the minimum sum value. Advantageously, this allows the user to prioritize between delivery efficiency and target conformity.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

FIG. 1 is a beams eye view ("BEV") of a target looking through a MLC;

FIG. 2 is a beams eye view through a MLC of a target according to an embodiment of the present invention;

FIG. 8 is a table illustrating results of a non-clinical treatment plan with a cube target;

FIG. 9 is a table of results for a non-clinical treatment plan with an ellipsoid target;

DETAILED DESCRIPTION OF THE INVENTION

The present invention will now be described more fully hereinafter with reference to the accompanying drawings, which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout. Prime notation, if used, indicates similar elements in alternative embodiments.

Figure 17:
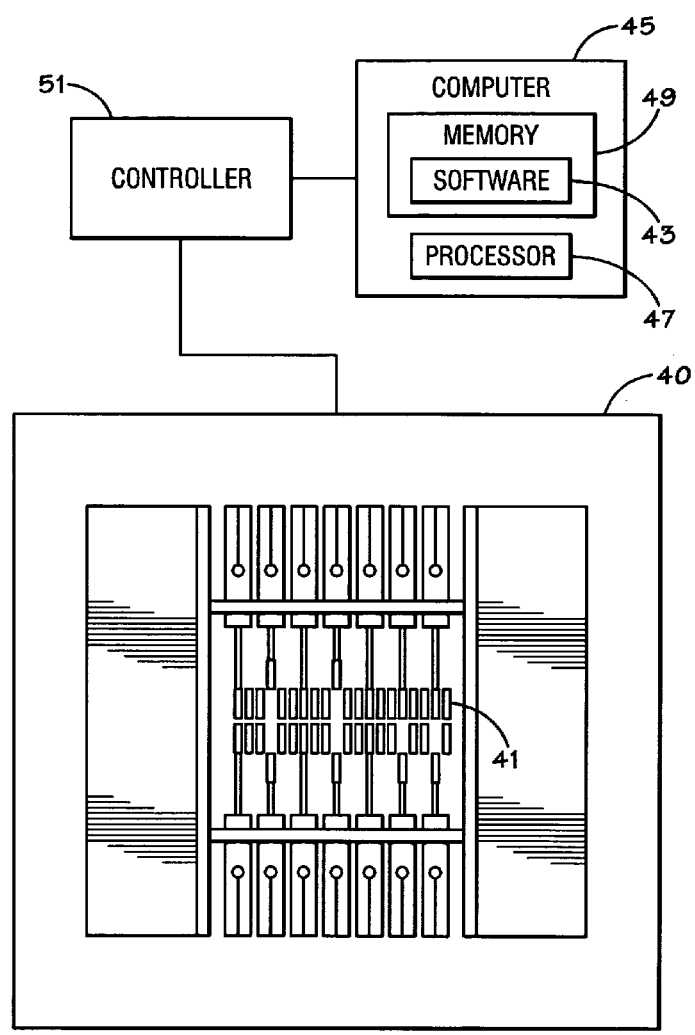
FIG. 17 is a cross-sectional view of the MLC illustrating leafs forming a plurality of radiation beam segments.

FIG. 1 illustrates the desired results of a presently used treatment plan using an algorithm based upon Brahme's theory, wherein the conformity for targets, or lesions, 20 is prioritized. Present treatment planning systems mathematically minimize the area between the frame 21 shaped by a conventional MLC opening and the edge of the target 20. Multi-leaf collimators (MLCs) currently in use with which the present invention may be utilized, such as, for example, the multi-leaf collimator 40 depicted in FIG. 17, include, among others, MLCs manufactured and/or distributed by Varian Medical Systems, Inc., such as its Millennium MLC Models No. MLC-120, MLC-80, and MLC-52, which correspond to MLCs having 120, 80, and 52 leaves; and/or MLCs of Siemens AG and/or Siemens Medical Systems, Inc.

The algorithm utilized in embodiments of the present invention is based upon two hypotheses: (1) that the maximum number of segments in a radiation beam is dominated, or determined, by the MLC leaf pair of a plurality of leaf pairs 41 (FIG. 17) which delivers the maximum number of beamlets, or radiation beamlets; and (2) that the number of segments in a pair of MLC leaves is proportional to an effective leaf travel distance (the number of pencil beamlets) defined by:

$$le = \left(1 + \frac{n-1}{k}\right)\sum_{i=1}^{n} m_i$$

wherein n is the number of separated target regions in the path of the MLC leaf pair, or leaf travel distance of an individual MLC leaf pair; $m_i$ is the leaf travel distance in the ith isolated target region for the MLC leaf pair; and k is the weight factor to account for multi isolated regions in the path over which the MLC leaf pair sweeps.

In the algorithm used in embodiments of the present invention, the collimator angles are chosen so that the maximum amount of movement in individual MLC leaf pairs, at a certain collimator angle, is a minimum, as the maximum number of segments in a beam is largely determined by the MLC leaf pair which performs the maximum number of segments. The cost function to favor, or enhance, delivery efficiency, the reduction of segments, in determination of the collimator angle is:

$$f(\theta_o) = \min\{\max l_e(\theta)]\}$$

where (θ) is the collimator angle varying from 0 to 180, 1 degree/step, and ($\theta_o$), is the optimized angle.

The procedure is to search the maximum effective length of MLC pairs in a certain collimator angle, and then find the minimum values from, in this example, the 180 maximum effective lengths. Combining the new algorithm utilized in embodiments of the present invention with the algorithm based upon Brahme's theory, the cost function to determine the collimator angle is:

$$f(\theta_o) = \min\{A \max[l_e(\theta)] + B\sigma(\theta)\}$$

where σ(θ) is the area difference between what an MLC can define and the target area, and A and B are weight factors used in the algorithm to select a focus between delivery efficiency and conformity.

The computations associated with the cost function to determine the optimum collimator angle and related software 43 (FIG. 17) can be processed on a computer or other computational device known to those skilled in the art and which can be associated with the selected radiation delivery apparatus. For example, computer 45 (FIG. 17) generally having a processor 47 and memory 49, and software 43 stored in the memory 49, can be used for such purpose. Computer 45 can include various input devices and/or displays (not shown) or function as a server connected to a remote terminal. Computer 45 is typically connected to a controller 51 to control the multi-leaf collimator 40. Further, the software 43 to perform such computations can be stored on various other forms of storage media known to those skilled in the art, such as, for example, computer hard drives, compact discs, and removable drives, and is preferably associated with the treatment planning software.

With reference to FIG. 2, the area, which the MLC can define, is outlined by lines 30, which is the rectangular shaped area defined by the MLC leaves, and the target area 31 is shown as having an irregular shape defined by lines 32.

The user of the method and apparatus of embodiments of the present invention can choose what is preferred by adjusting the weight factors A and B. For example, radiation treatment plans using intensity modulated radio surgery ("IMRS") may prefer to treat a patient with a system utilizing the algorithm based upon Brahme's theory. Alternatively, in a radiation therapy treatment plan for a large target or targets, the reduction of the number of segments and MUs might be prioritized.

Figure 3:
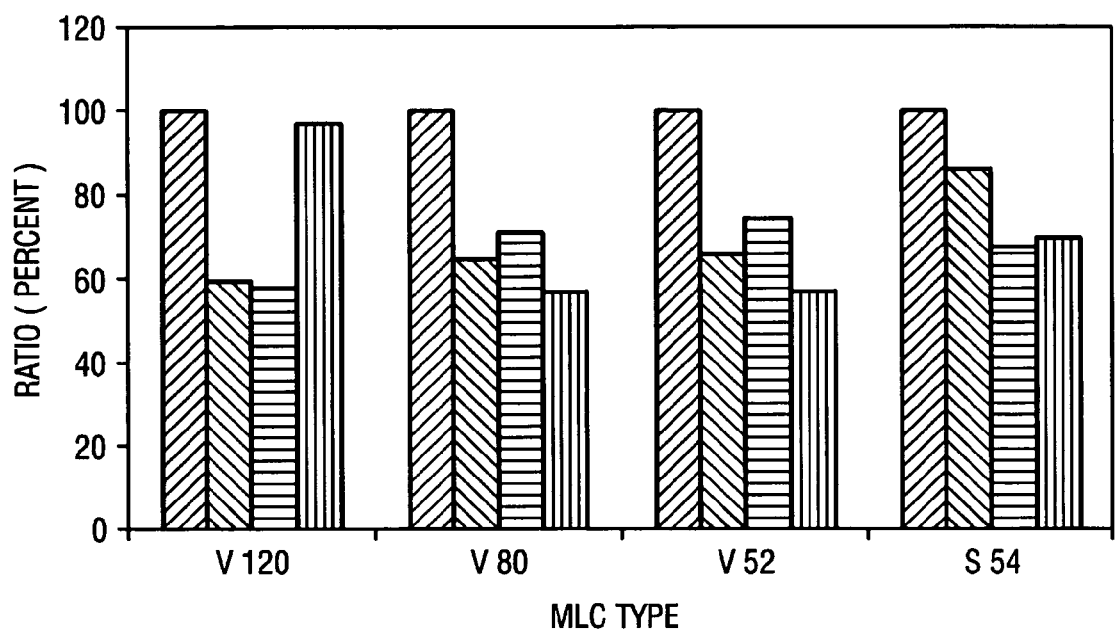
FIG. 3 is a chart comparing the number of segments and MUs between radiation therapy treatment plans using the prior art and the present invention.
Figure 4:
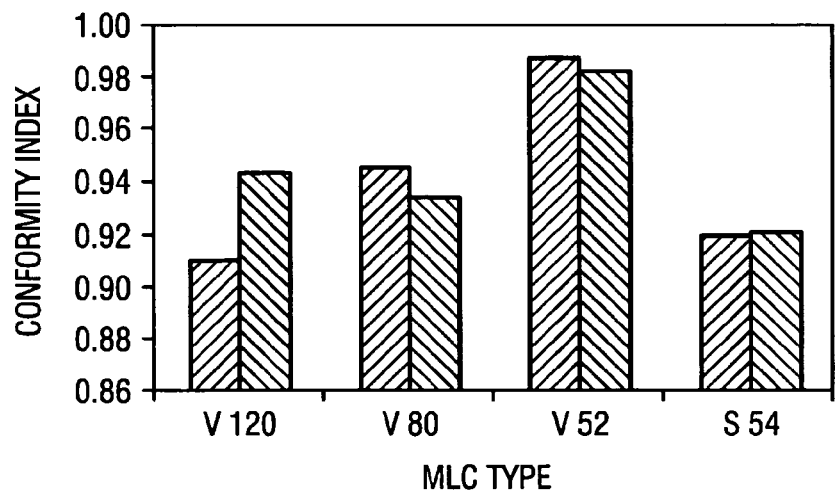
FIG. 4 is a chart comparing prostate conformity index between radiation therapy treatment plans using the prior art and the present invention.
Figure 5:
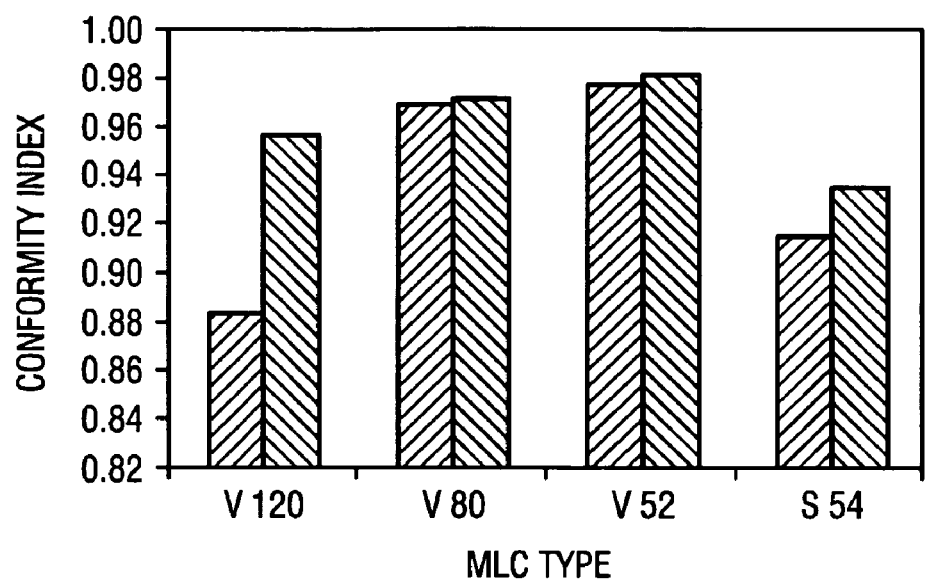
FIG. 5 is a chart of a comparison of a seminal vesicle conformity index between radiation therapy treatment plans using the prior art and the present invention.
Figure 6:
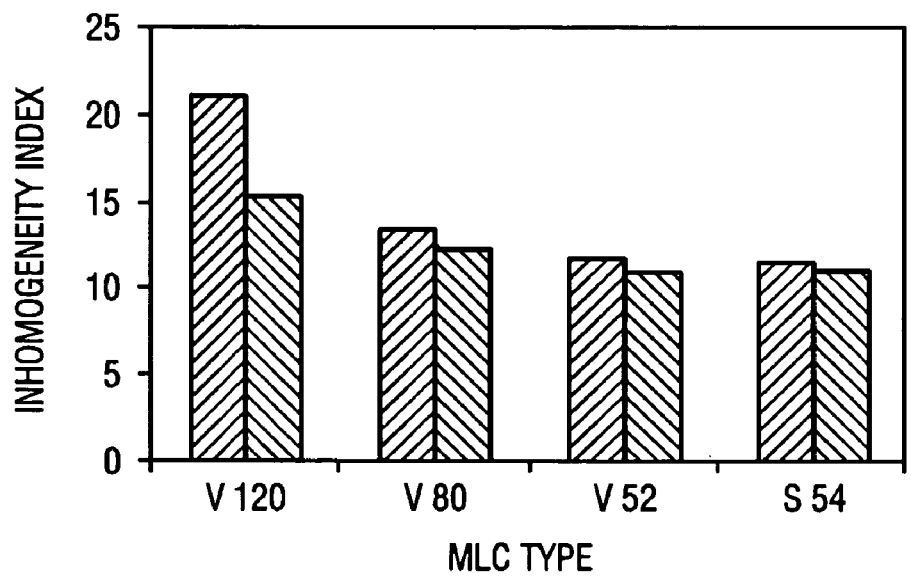
FIG. 6 is a chart of a comparison of seminal vesicles inhomogenity index between radiation therapy treatment plans using the prior art and the present invention.
Figure 7:
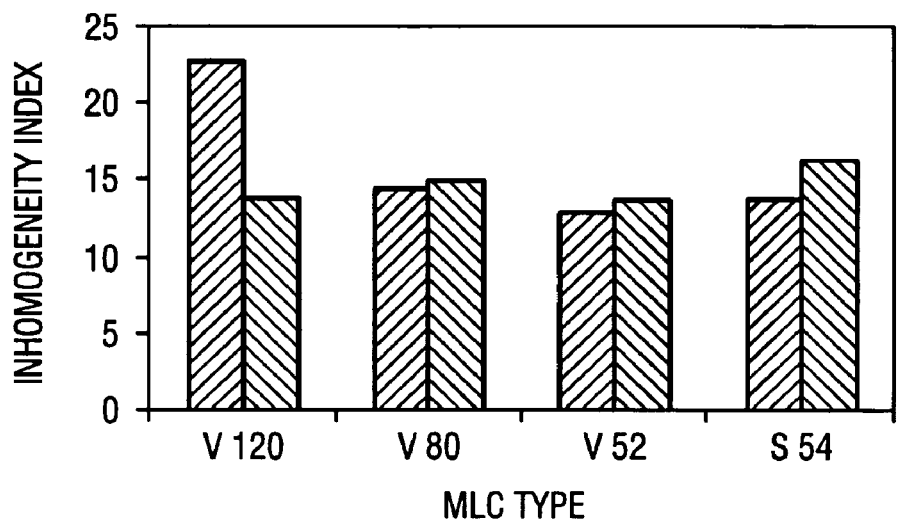
FIG. 7 is a chart of a comparison of prostate inhomogenity index between radiation therapy treatment plans using the prior art and the present invention.

The reduction of the number of segments and MUs, which are indicative of IMRT delivery efficiency, relies upon the shape and size of the target or targets, and the number of modulation levels utilized. For example, the following illustrates a case for the treatment of prostate cancer, two targets (the prostate and the seminal vesicles) and three organs at risk ("OAR"s) (the rectum, bladder, and femoral heads) are contoured. Seven radiation beams, ten modulation levels, and a six MV linear accelerator are used. Utilizing the method and apparatus of the present invention, the number of segments was reduced forty-two (42%) percent, twenty-nine (29%) percent, and twenty-six (26%) percent and the number of MUs were reduced forty-one (41%) percent, thirty-five (35%) percent and thirty-four (34%) percent, when 102 leaf, 80 leaf, and 52 leaf MLCs of Varian Medical Systems, Inc., were used, respectively, as shown in FIG. 3. In FIG. 3, the number of MUs and segments, as well as angle differences from IMRT treatment plans utilizing the method and apparatus of the present invention, including the new algorithm, are compared with treatment plans utilizing the algorithm based upon Brahme's theory. In FIG. 3, all values are normalized by the values used in the treatment plan with Brahme's algorithm.

Still with reference to FIG. 3, the comparison includes a thirty two (32%) percent segment reduction and an MU reduction of fourteen (14%) percent with a Siemens MLC utilizing IMFAST® computer software of Siemens Medical Systems, Inc. It can also be seen that the larger the angle differences between plans utilizing the two algorithms, the greater reduction of the number of segments of MUs. Still with reference to FIG. 3, the "angle difference" is defined as the ratio of the collimator angle difference in the treatment plans utilizing the new algorithm and the Brahme's algorithm to that 90 times the number of beams.

With reference to FIGS. 4–7, a comparison of IMRT radiation treatment plans using the method and apparatus of the present invention, including the new algorithm, as compared with a treatment planning system using the Brahme's algorithm is illustrated in terms of target conformity and inhomogeneity indexes.

Two sets of IMRT radiation therapy treatment plans were generated with two target shapes, a cube and an ellipsoid. The number of segments and MUs were compared when the collimator angle was set at either where the $l_e$ was a minimum or a maximum. The amount of segmentation and MU reduction which can be achieved by manipulating the collimator angle alone are illustrated in connection with FIGS. 8 and 9 for different MLC leaf-sequencing algorithms and different sizes of the pencil beamlets, as will be hereinafter described in greater detail.

Figure 10:
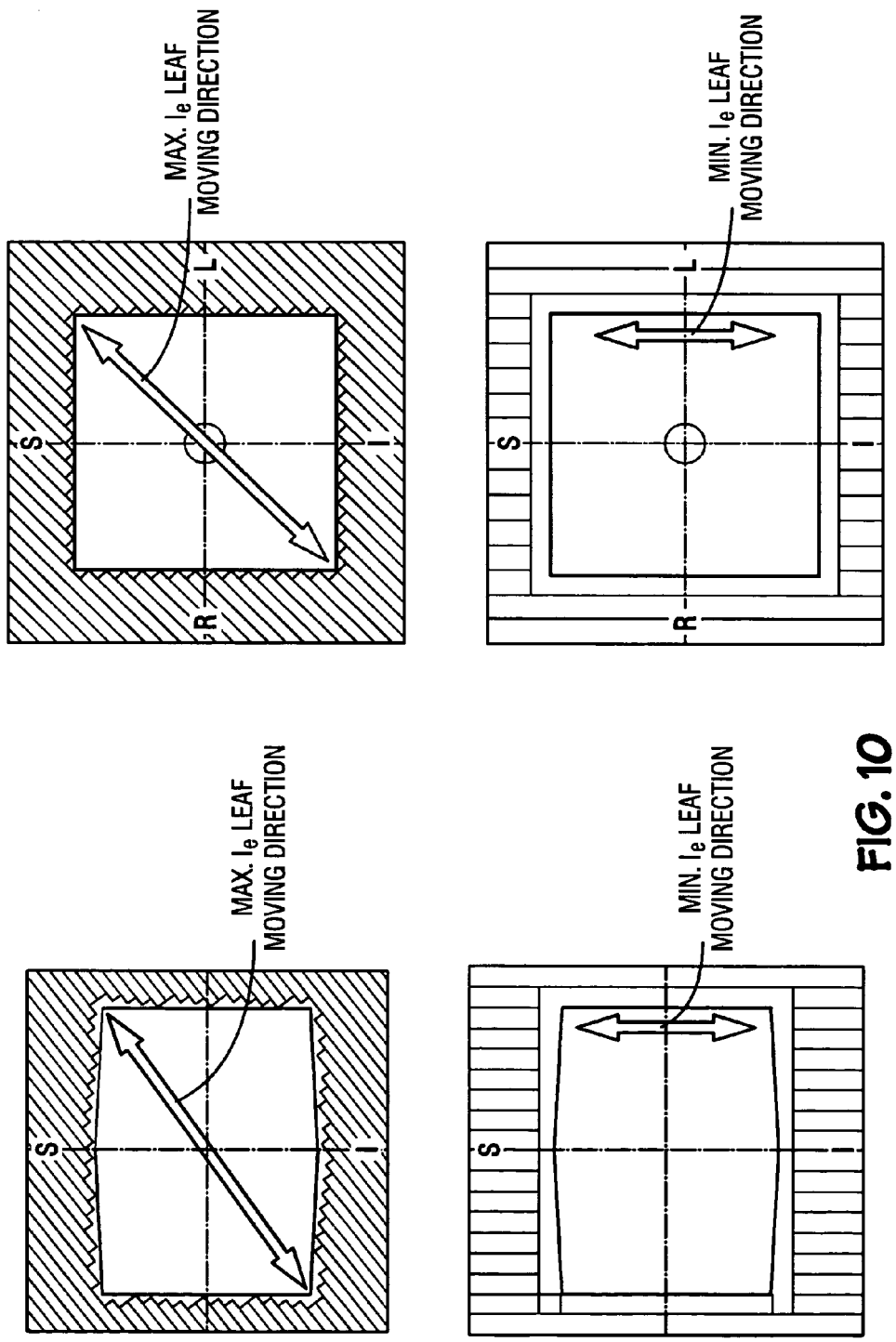
FIG. 10 are BEVs of a cube as a target.
Figure 11:
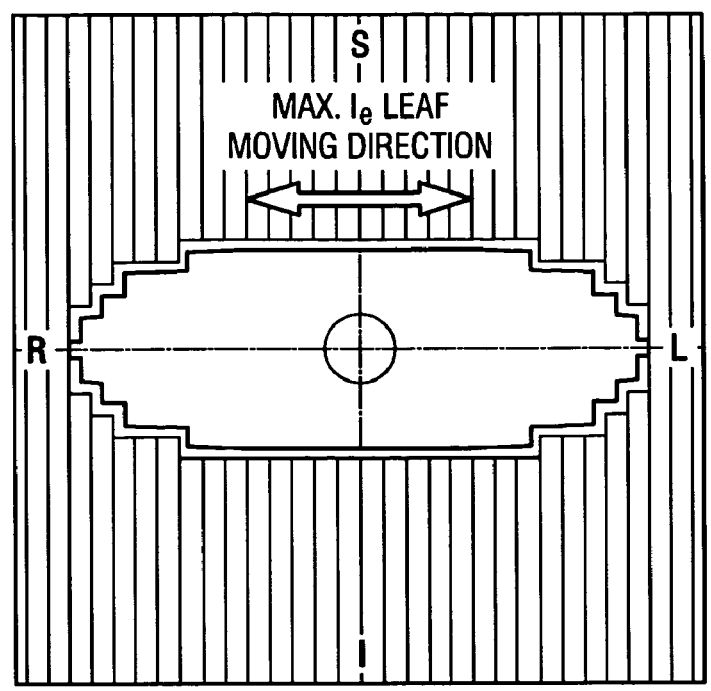
FIG. 11 are BEVs of an ellipsoid as a target.
Figure 11:
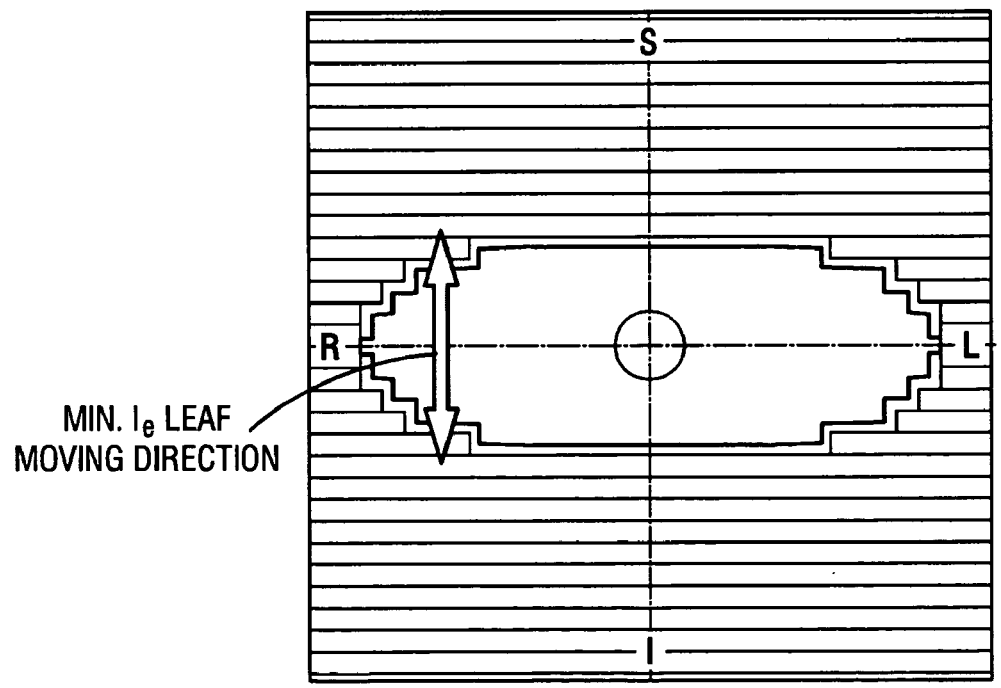

In the beams eye view ("BEV") of the collimator, as shown in FIGS. 10 and 11, a three dimensional target, such as a cube or ellipsoid, are projected onto two dimensions. The shortest dimension of the target is along the axis when θ=0. The IMRT radiation therapy treatment planning system utilized in connection with FIGS. 8–11 is a CORVUS®5 planning system of NOMOS Corporation. When the collimator angle is set at 0, the MLC leafs move along 90 degrees in the IEC coordinate system utilized by CORVUS®5. The target in both sets of plans was prescribed a dosage of 2Gy and with no margin for uncertainties. The optimizer of the CORVUS®5 was a continuous annealer. The first set of plans used a 100 mm cube as a target, with no OARs. The gantry angles were chosen so that the projections of the cube in the BEV have different dimension ratios (minimum dimension/maximum dimension). Five beams were used at gantry angles of 0, 67, 85, 135, and 169 degrees, which correspond to dimension ratios of 1.4, 1.6, 1.7, 1.5, and 1.47. The collimator angles in the plans when $l_e$ is a minimum or 90 degrees while 45, 41, 38, 43, and 44 degrees resulted in maximum $l_e$. The results for the first set of treatment plans with a cube target are set forth in the table of FIG. 8, in which the ratio is defined as the value at the collimator angle when $l_e$ is a minimum divided by that when $l_e$ is a maximum. For the treatment plans with an ellipsoid target, the results are summarized in the table of FIG. 9. The treatment plan formulated with the STANDARD™ leaf-sequencing algorithm for a 120 leaf MLC of Varian Medical Systems, Inc. (0.5×0.5 cm pencil beamlet) and a Varian 80 leaf MLC (1×1 cm beamlet) have the largest segmentation and MU reduction (34 percent and 26 percent, respectively) when setting the collimator angle with the algorithm utilized in the method and apparatus of the present invention. When the treatment plan is based upon the IMFAST® leaf-sequencing algorithm of Siemens with a Siemens 54 leaf MLC, the reduction of segments and MUs is less significant.

In connection with clinical case studies, the following parameters are hereinafter defined below:

$$Mu\ Ratio\ \frac{\text{No. MU in the plan using the new algorithm}}{\text{No. MU in the plan using Brehme's}}$$

$$Seg.\ Ratio\ \frac{\text{No. Segments in the plan with the new algorithm}}{\text{No. Segments in the plan using Brehme's}}$$

$$Angle\ similarity = \left(1 - \frac{Colli.angle difference}{90 * no.of beams}\right) * 100\%$$

Figure 12:
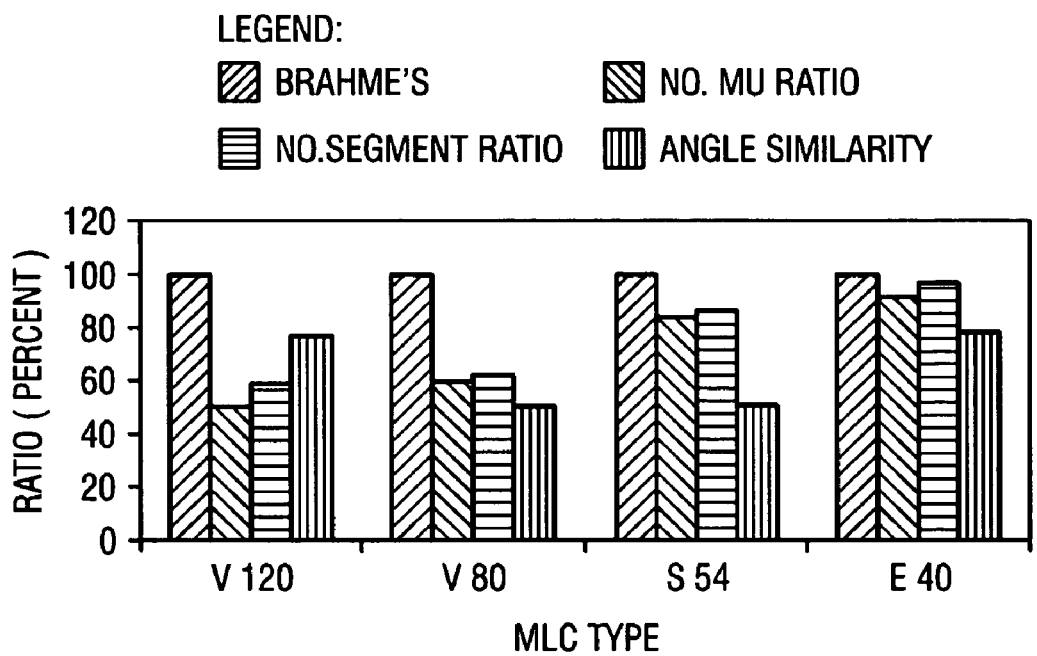
FIG. 12 is a chart comparing the number of segments and MUs between radiation therapy treatment plans using the prior art and the present invention.

To further illustrate the advantages of the method and apparatus of the present invention incorporating the new algorithm, FIGS. 12–16 show the results of two clinical cases which were investigated, those being a prostate and a complicated head and neck case. The prostate case had two targets, the prostate and seminal vesicles, and three OARs, which were the bladder, rectum, and femoral heads. The total target volume was 170 cc. Seven beams and eleven modulation levels were used. The optimizer again was a continuous annealer and no margin was given to the targets and OARs. In the prostate plan, the collimator angle similarity was defined by:

$$\left(1 - \frac{\sum_{i=1}^{j} \theta i}{90 * j}\right) * 100$$

where ($\theta_j$) is the collimator angle difference at individual gantry angles between using the Brahme's algorithm and the algorithm of the present invention, and j is the number of beams. With reference to FIG. 12, a comparison is illustrated of the ratio of the number of MUs, segments, and collimator angle similarity between the plan using Brahme's algorithm and that using the algorithm of the present invention, all values normalized by the values of the plan with Brahme's algorithm. The number of MUs and segments has been reduced dramatically utilizing the method and apparatus of the present invention incorporating the new algorithm.

Figure 13:
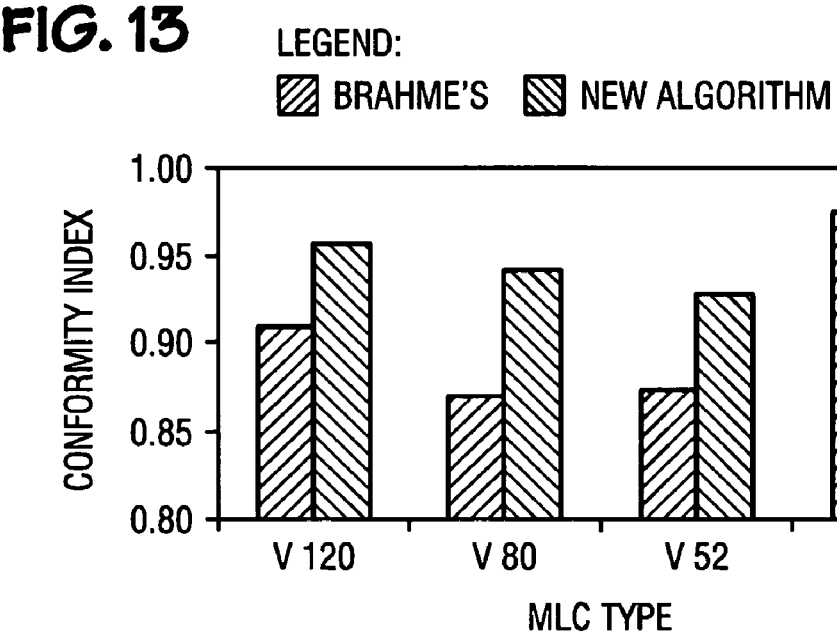
FIG. 13 is a chart comparing the conformity index of a prostate between radiation therapy treatment plans using the prior art and the present invention.
Figures 14, 15:
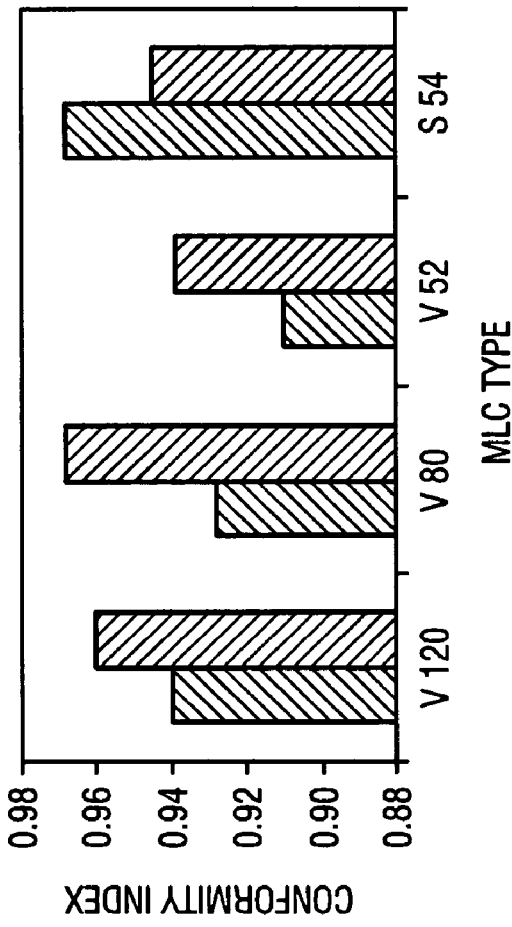
FIG. 14 is a comparison of a conformity index for seminal vesicles between radiation therapy treatment plans using the prior art and the present invention.
FIG. 15 is a table summarizing the results of the charts of FIGS. 13 and 14.

The target conformity indexes ("CI") for both prostate and seminal vesicles are illustrated in the graphs of FIGS. 13 and 14, and in tabular form in FIG. 15. The improvement in conformity index for MLC's directed by treatment plans using the new algorithm was more significant for MLCs directed by treatment plans utilizing the Brahme's algorithm and having a lower conformity index.

Figure 16:
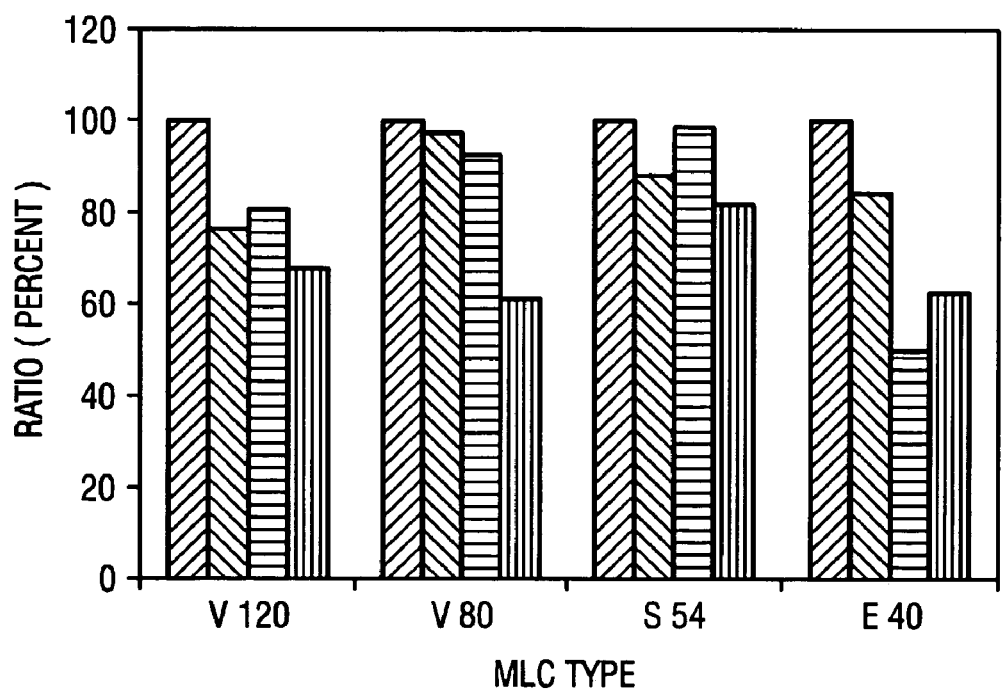
FIG. 16 is a comparison of the number of segments and MUs when utilizing the prior art and the present invention.

In the complicated head and neck case, three large targets, totaling approximately 490 cc, with 12 OARS, were the subject of an IMRT treatment plan. Seven beams and a continuous annealer were used. Eleven modulation levels were utilized, and no margin was given to either targets or OARS. The maximum dimension of the targets was 23.5 cm. The comparison of the number of MUs and segments, as well as the collimator angle similarity, is illustrated in the graph of FIG. 16. The less the collimator angle similarity, the more significant the reduction in MUs and segments with a treatment plan incorporating the new algorithm.

In view of the foregoing non-clinical and clinical examples, it is seen that the method and apparatus of the present invention, utilizing the new algorithm herein, can reduce the number of segments and MUs without compromising the treatment plan quality. The reduction of the number of segments and MUs is generally more effective for: (1) the STANDARD™ leaf-sequencing algorithm based on the work of Bortfeld for the Varian MLC; (2) large targets; and (3) small pencil beamlets. The results from the non-clinical and clinical cases would appear to show that treatment plans using the IMFAST® leaf-sequencing algorithm do not obtain as much reduction of MUs and segments as those using the STANDARD™ algorithm.

Advantageously, since the algorithm of the method and apparatus of the present invention minimizes the maximum leaf travel distance, the application of the algorithm to dynamic MLC delivery (sweeping algorithm based on Borfeld's work) and direct aperture optimization ("DAO") would possibly lead to faster IMRT plan delivery.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims. For example, the discussion primarily focused determining a rotational angle of the multi-leaf collimator for a beam delivery iteration at a single radiation beam delivery angle (gantry angle of rotation for a linear accelerator). In practice, multiple beam delivery iterations at varying radiation beam delivery angles are required for a single radiation treatment session according to a radiation treatment plan.

The invention claimed is:

1. A computer-implemented method of determining a collimator angle of a multi-leaf collimator having an opening and a plurality of multi-leaf collimator leaf pairs for closing portions of the opening to form a radiation beam arrangement having a plurality of radiation beam segments to apply radiation to a tumor target, the method comprising the steps of:
   calculating an initial radiation beam arrangement according to a desired prescription; and
   changing the radiation beam arrangement by incorporating a first cost function to determine the collimator angle of the multi-leaf collimator, the first cost function including both a second cost function to enhance delivery efficiency by reducing a number of radiation beam segments and reducing a number of radiation beam monitor units required for delivery of the desired prescription and a third cost function to enhance conformity of the radiation beam arrangement to a target shape.

2. A method as defined in claim 1, wherein the first cost function is obtained by performing the steps of:
   determining for each one of a plurality of discrete collimator angles a value of an area difference between an area of the opening in the multi-leaf collimator which the multi-leaf collimator can define when approaching correspondence with the target shape in a beams eye view of the multi-leaf collimator and an area of the target shape in the same beams eye view of the multi-leaf collimator, a view from the perspective of the opening in the multi-leaf collimator along an axis of the radiation beam defining the beams eye view of the multi-leaf collimator;
   determining for each one of the plurality of discrete collimator angles a value of a maximum effective length for a multi-leaf collimator leaf pair of the plurality of multi-leaf collimator leaf pairs having the maximum effective length;
   determining a sum of the value of the area difference and the value of the maximum effective length for each of the plurality of discrete collimator angles; and
   determining a minimum sum value for the sum of the value of the area difference and the value of the maximum effective length for a collinear angle of the plurality of collimator angles having the minimum sum value.

3. A method as defined in claim 2, further comprising the steps of:
   selecting a first weight value for the maximum effective length and a second weight value for the area difference, selection criteria including a type of radiation delivery system carrying the multi-leaf collimator and a size and shape of the target; and
   applying the first weight value to the maximum effective length and the second weight value to the area difference prior to determining the minimum sum value.

4. A method as defined in claim 1, further comprising the step of:

rejecting the change in the radiation beam arrangement if the change of the radiation beam arrangement significantly leads to a lesser correspondence to the desired prescription and accepting the change of the radiation beam arrangement if the change of the radiation beam arrangement both leads to more radiation delivery efficiency and does not lead to significantly less correspondence to the desired prescription.

5. A method as defined in claim 1, wherein the first cost function is obtained by the steps of:

determining for each one of a plurality of discrete collimator angles a weighted value of an area difference between an area of the opening in the multi-leaf collimator which the multi-leaf collimator can define when approaching correspondence with the target shape in a beams eye view of the multi-leaf collimator and an area of the target shape in the same beams eye view of the multi-leaf collimator, according to the formula:

$$B\sigma(\theta)$$

where $\sigma(\theta)$ is the third cost function describing the area difference between what an multi-leaf collimator can define and the target area, B is a weight factor, and $\theta$ is the collimator angle which varies by discrete increments;

determining for each one of the plurality of discrete collimator angles a weighted value of a maximum effective length for a multi-leaf collimator leaf pair of the plurality of multi-leaf collimator leaf pairs having the maximum effective length, according to the following formula:

$$A \max[l_e(\theta)]$$

where $\max[l_e(\theta)]$ is the second cost function describing the maximum effective length for a multi-leaf collimator leaf pair of the plurality of multi-leaf collimator leaf pairs having the maximum effective length, A is a weight factor, and $l_e$ is determined according to the following formula:

$$le = \left(1 + \frac{n-1}{k}\right)\sum_{i=1}^{n} m_i$$

where n is the number of separated target regions in the path of the multi-leaf collimator leaf pair, $m_i$ is the leaf travel distance in the ith isolated target region for the multi-leaf collimator leaf pair, and k is the weight factor to account for multi-isolated regions in the path over which the multi-leaf collimator leaf pair sweeps;

determining a sum of the weighted value of the area difference and the weighted value of the maximum effective length for each of the plurality of discrete collimator angles; and determining a minimum sum value for the sum of the value of the area difference and the value of the maximum effective length for a collinear angle of the plurality of collimator angles having the minimum sum value, according to the following formula:

$$f(\theta_o) = \min\{A \max[l_e(\theta)] + B\sigma(\theta)\}$$

where $\theta_o$ is the optimized collimator angle.

6. A method of determining a collimator angle of a multi-leaf collimator having an opening and a plurality of multi-leaf collimator leaf pairs for closing portions of the opening to form a radiation beam arrangement having a plurality of radiation beam segments to apply radiation to a tumor target, the method comprising the steps of:

determining a treatment plan according to a desired prescription;

determining for each one of a plurality of discrete collimator angles a value of an area difference between an area of the opening in the multi-leaf collimator which the multi-leaf collimator can define when approaching correspondence with the target shape in a beams eye view of the multi-leaf collimator and an area of the target shape in the same beams eye view of the multi-leaf collimator;

determining for each one of the plurality of discrete collimator angles a value of a maximum effective length for a multi-leaf collimator leaf pair of the plurality of multi-leaf collimator leaf pairs having the maximum effective length;

determining a sum of the value of the area difference and the value of the maximum effective length for each of the plurality of discrete collimator angles;

determining a minimum sum value for the sum of the value of the area difference and the value of the maximum effective length for the collimator angle of the plurality of collimator angles having the minimum sum value; and selecting for application to the treatment plan prior to treatment plan optimization, the collimator angle having the minimum sum value.

7. A method as defined in claim 6, further comprising the step of:

selecting a first weight value for the maximum effective length and a second weight value for the area difference; and applying the first weight value to the maximum effective length and the second weight value to the area difference prior to determining the minimum sum value.

8. A method as defined in claim 7, wherein the step of selecting a first weight and a second weight further comprises the steps of:

determining a type of radiation delivery system carrying the multi-leaf collimator; and determining a size and shape of the target.

9. A method as defined in claim 7, wherein the step of selecting a first weight and a second weight further comprises the step of:

selecting a preference between delivery efficiency and target conformity by applying separate first and second weight values to the maximum effective length and area difference, respectively.

10. A method of determining a collimator angle of a multi-leaf collimator having an opening and a plurality of multi-leaf collimator leaf pairs for closing portions of the opening to form a radiation beam arrangement having a plurality of radiation beam segments to apply radiation to a tumor target, the method comprising the steps of:

providing a cost function having a first delivery efficiency portion providing for enhanced radiation delivery efficiency and a second target conformity portion providing for enhanced target conformity;

determining a type of radiation delivery system carrying the multi-leaf collimator;

determining a size and a shape of the target;

selecting a preference between delivery efficiency and target conformity responsive to the determination of the type of radiation delivery system and the size and the shape of the target;

determining a value for the cost function at a selected radiation beam delivery angle incorporating the selected preference; and responsive to the value of the cost function, determining the collimator angle.

11. A method as defined in claim 10, wherein the step of selecting a preference includes the step of assigning separate weight values to the first delivery efficiency portion of the cost function and to the second target conformity portion of the cost function.

12. A method as defined in claim 11, wherein the first delivery efficiency portion of the cost function includes a delivery efficiency cost function that determines at each of a plurality of discrete collimator angles a weighted value of a maximum effective length for a multi-leaf collimator leaf pair of the plurality of multi-leaf collimator leaf pairs having the maximum effective length, and wherein the second target conformity portion of the cost function includes a target conformity cost function that determines at each of a plurality of discrete collimator angles a weighted value of an area difference between an area of the opening in the multi-leaf collimator which the multi-leaf collimator can define when approaching correspondence with the target shape in the beams eye view of the multi-leaf collimator and an area of the target shape in the same beams eye view of the multi-leaf collimator.

13. A computer readable medium that is readable by a computer determining a collimator angle of a multi-leaf collimator having an opening and a plurality of multi-leaf collimator leaf pairs for closing portions of the opening to form a radiation beam arrangement having a plurality of radiation beam segments to apply radiation to a tumor target, the computer readable medium comprising a set of instructions that, when executed by the computer, causes the computer to perform the following operations:
    determine a treatment plan according to a desired prescription;
    determine for each one of a plurality of discrete collimator angles a value of an area difference between an area of the opening in the multi-leaf collimator which the multi-leaf collimator can define when approaching correspondence with the target shape in the beams eye view of the multi-leaf collimator and an area of the target shape in the same beams eye view of the multi-leaf collimator;
    determine for each one of the plurality of discrete collimator angles a value of a maximum effective length for a multi-leaf collimator leaf pair of the plurality of multi-leaf collimator leaf pairs having the maximum effective length;
    determine a sum of the value of the area difference and the value of the maximum effective length for each of the plurality of discrete collimator angles;
    determine a minimum sum value for the sum of the value of the area difference and the value of the maximum effective length for a collimator angle of the plurality of collimator angles having the minimum sum value; and
    select for application to the treatment plan prior to treatment plan optimization, the collimator angle having the minimum sum value.

14. A computer readable medium according to claim 13, further comprising the following set of instructions:
    receive from a user a first weight value for the maximum effective length and a second weight value for the area difference; and
    apply the first weight value to the maximum effective length and the second weight value to the area difference prior to determining the minimum sum value.

15. A computer readable medium according to claim 14, further comprising the following set of instructions:
    determine a type of radiation delivery system carrying the multi-leaf collimator; and
    determine a size and shape of the target.

16. A computer readable medium according to claim 14, further comprising the following instruction:
    select a preference between delivery efficiency and target conformity by applying separate user defined first and second weight values to the maximum effective length and area difference, respectively.

17. An apparatus for use in conformal radiation therapy of a target tumor, the apparatus comprising:
    a multi-leaf collimator having a plurality of selectable discrete collimator angles, an opening to pass a radiation beam, and a plurality of multi-leaf collimator leaf pairs to close portions of the opening to form a radiation beam arrangement having a plurality of radiation beam segments; and
    a computer in communication with the multi-leaf collimator to form the radiation beam arrangement incorporating a cost function to determine a collimator angle of the multi-leaf collimator to thereby enhance the radiation beam arrangement, the cost function including both parameters to enhance conformity of the radiation beam arrangement to a shape of the target, and parameters to enhance delivery efficiency by reducing a number of segments and reducing a number of monitor units required for delivery of a desired radiation prescription.

18. An apparatus as defined in claim 17, wherein the parameters to enhance delivery efficiency include a value of a maximum effective length for a multi-leaf collimator leaf pair of the plurality of multi-leaf collimator leaf pairs having the maximum effective length.

19. An apparatus as defined in claim 18, wherein the parameters to enhance conformity of the radiation beam arrangement include an area difference between an area of an opening in the multi-leaf collimator which the multi-leaf collimator can define when approaching correspondence with a target shape in a beams eye view of the multi-leaf collimator and an area of the target shape in the same beams eye view of the multi-leaf collimator, a view from the perspective of the opening in the multi-leaf collimator along an axis of the radiation beam defining the beams eye view of the multi-leaf collimator.

20. An apparatus as defined in claim 19, wherein the cost function provides a minimum sum value for the sum of the value of the area difference and the value of the maximum effective length for the collimator angle of the plurality of collimator angles having the minimum sum value.

21. An apparatus as defined in claim 20, further comprising:
    means for selecting a first weight value for the maximum effective length and a second weight value for the area difference; and
    means for applying the first weight value to the maximum effective length and the second weight value to the area difference prior to determining the minimum sum value.

* * * * *